(12) United States Patent
Maxey et al.

(10) Patent No.: US 6,316,468 B1
(45) Date of Patent: Nov. 13, 2001

(54) PHENYLINDOLE DERIVATIVES AS 5-HT$_{2A}$ RECEPTOR ANTAGONISTS

(75) Inventors: Robert James Maxey, Amersham; Michael Rowley, Chelmsford; Monique Bodil Van Niel, Welwyn Garden City, all of (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 09/486,846

(22) PCT Filed: Aug. 25, 1998

(86) PCT No.: PCT/GB98/02552

§ 371 Date: Mar. 1, 2000

§ 102(e) Date: Mar. 1, 2000

(87) PCT Pub. No.: WO99/11641

PCT Pub. Date: Mar. 11, 1999

(30) Foreign Application Priority Data

Sep. 3, 1997 (GB) .................................................. 9718712

(51) Int. Cl.$^7$ ....................... A61K 31/445; C07D 401/00
(52) U.S. Cl. ...................... 514/321; 514/323; 546/197; 546/201
(58) Field of Search ................... 546/201, 147; 514/323, 321

(56) References Cited

U.S. PATENT DOCUMENTS 5,457,115 * 10/1995 Perregaard et al. ................. 514/323
5,703,070   12/1997 Lavielle et al. .................... 514/212

FOREIGN PATENT DOCUMENTS 0 747 379   12/1996 (EP) .
1465826     3/1977  (GB) .
3264581     11/1991 (JP) .
A-3-264581  11/1991 (JP) .
WO 91/18602 12/1991 (WO) .

OTHER PUBLICATIONS

D. C. Dyer, Life Sciences, 1993, 53, pp. 223–228.

\* cited by examiner

Primary Examiner—Alan L. Rotman
Assistant Examiner—Raymond Covington
(74) Attorney, Agent, or Firm—James L. McGinnis; David L. Rose

(57) ABSTRACT

3-(Piperidin-4-yl)-1H-indole derivatives bearing an optionally substituted phenyl moiety at the 2-position of the indole ring system and an alkyl or aryl-alkyl substituent on the nitrogen atom of the piperndine ring are selective antagonists of the human 5-HT$_{2A}$ receptor.

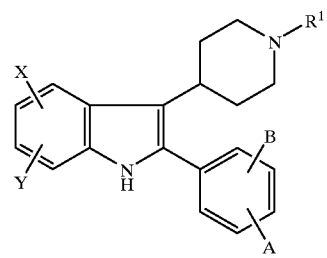

(I)

They are therefore useful as pharmaceutical agents, especially in the treatment and/or prevention of adverse conditions of the central nervous system, including psychotic disorders such as schizophrenia.

13 Claims, No Drawings

PHENYLINDOLE DERIVATIVES AS 5-HT$_{2A}$ RECEPTOR ANTAGONISTS

The present invention relates to a class of indole derivatives which act on serotonin receptors (also known as 5-hydroxytryptamine or 5-HT receptors). More particularly, the invention concerns 3-(piperidin-4-yl)-1H-indole derivatives bearing an optionally substituted phenyl moiety at the 2-position of the indole ring system and an alkyl or arylalkyl substituent on the nitrogen atom of the piperidine ring. These compounds are selective antagonists of the human 5-HT$_{2A}$ receptor and are therefore useful as pharmaceutical agents, especially in the treatment and/or prevention of adverse conditions of the central nervous system, including psychotic disorders such as schizophrenia.

Schizophrenia is a disorder which is conventionally treated with drugs known as neuroleptics. In many cases, the symptoms of schizophrenia can be treated successfully with so-called "classical" neuroleptic agents such as haloperidol. Classical neuroleptics generally are antagonists at dopamine D$_2$ receptors.

Notwithstanding their beneficial antipsychotic effects, classical neuroleptic agents such as haloperidol are frequently responsible for eliciting acute extrapyramidal symptoms (movement disorders) and neuroendocrine (hormonal) disturbances. These side-effects, which plainly detract from the clinical desirability of classical neuroleptics, are believed to be attributable to D$_2$ receptor blockade in the striatal region of the brain.

The compound (+)-α-(2,3-dimethoxyphenyl)-1-[2-(4-fluorophenyl)-ethyl]-4-piperidinemethanol (also known as MDL-100,907) is described in WO 91/18602. In preclinical studies, MDL-100,907 failed to induce catalepsy and failed to block apomorphine-induced stereotyped behaviour in animal models, strongly suggesting that this compound would be free from any liability to cause extrapyramidal side-effects. MDL-100,907 is currently undergoing clinical trials in schizophrenic patients and has demonstrated efficacy in a multicentre, placebo-controlled study for antipsychotic potential, with no neurological adverse effects. Pharmacologically, MDL-100,907 has been shown to be a potent antagonist of human 5-HT$_{2A}$ receptors, whilst being essentially devoid of activity at the human dopamine D$_2$ receptor. It is accordingly believed that compounds which can interact selectively with the 5-HT$_{2A}$ receptor relative to the dopamine D$_2$ receptor will display the beneficial level of antipsychotic activity associated with 5-HT$_{2A}$ receptor antagonism, whilst minimizing or even avoiding the extrapyramidal and other side-effects arising from an interaction with dopamine D$_2$ receptors.

The compounds of the present invention are potent antagonists of the human 5-HT$_{2A}$ receptor, and are accordingly of benefit in the treatment and/or prevention of psychotic disorders such as schizophrenia. The compounds of the invention may display more effective binding to the human 5-HT$_{2A}$ receptor than to the human dopamine D$_2$ receptor, and they can therefore be expected to manifest fewer side-effects than compounds which do not discriminate in their binding affinity as between 5-HT$_{2A}$ and D$_2$ receptors.

By virtue of their potent human 5-HT$_{2A}$ receptor antagonist activity, the compounds of the present invention are also effective in the treatment of neurological conditions including depression, anxiety, panic disorder, obsessive-compulsive disorder, pain, sleep disorders such as insomnia, eating disorders such as anorexia nervosa, and dependency or acute toxicity associated with narcotic agents such as LSD or MDMA; and cardiovascular conditions including variant angina, Raynaud's phenomenon, intermittent claudication, coronary and peripheral vasospasms, fibromyalgia, cardiac arrhythmias and thrombotic illness. They may also be generally of benefit in the inhibition of platelet aggregation, as well as in controlling the extrapyramidal symptoms associated with the administration of neuroleptic agents. They may further be effective in the lowering of intraocular pressure and may therefore be beneficial in treating glaucoma (cf. T. Mano et al. and H. Takaneka et al., *Investigative Ophthalmology and Visual Science*, 1995, vol. 36, pages 719 and 734 respectively).

Being 5-HT$_{2A}$ receptor antagonists, the compounds of the present invention may also be beneficial in preventing or reducing the toxic symptoms associated with the intake of ergovaline in animals consuming *Acremoniun coenophicalun* infected tall fescue (cf. D. C. Dyer, *Life Sciences*, 1993, 53, 223–228).

In JP-A-3-264581 is described a class of 3-(piperidin-4-yl)-1H-indole analogues bearing inter alia an optionally substituted phenyl group at the 2-position of the indole nucleus and a heterocyclic moiety attached through an alkylene linkage to the nitrogen atom of the piperidine ring. These compounds are stated therein to have a strong serotonin-2 receptor antagonist action and hence to be useful as medicines for the treatment of diseases of the circulatory system, and of psychiatric diseases such as depression or schizophrenia. There is, however, no disclosure nor any suggestion in JP-A-3-264581 of replacing the precisely defined heterocyclyl-alkyl substituent on the piperidine ring with an alkyl or aryl-alkyl moiety.

GB-1465826 describes a variety of indolylpiperidine-butyrophenones bearing inter alia a phenyl group at the 2-position of the indole ring system. These compounds are alleged therein to show activities typical of neuroleptics and therefore to be of potential interest as depressants of the central nervous system, as sedatives and as tranquilizers. However, nowhere in GB-1465826 is there any disclosure or suggestion of replacing the 4-fluorobutyrophenone substituent on the piperidine ring with an alkyl or aryl-alkyl moiety.

The compounds according to the present invention are potent and selective 5-HT$_{2A}$ receptor antagonists having a human 5-HT$_{2A}$ receptor binding affinity (K$_i$) of 100 nM or less, typically of 50 nM or less and preferably of 10 nM or less. The compounds of the invention may possess at least a 10-fold selective affinity, suitably at least a 20-fold selective affinity and preferably at least a 50-fold selective affinity, for the human 5-HT$_{2A}$ receptor relative to the human dopamine D$_2$ receptor.

The present invention provides a compound of formula I, or a salt thereof:

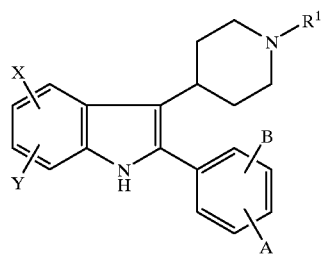

(I)

wherein
A and B independently represent hydrogen, halogen, cyano, nitro, trifluoromethyl, trifluoromethoxy, C$_{1-6}$ alkyl, C$_{1-6}$ alkoxy or amino; or A and B, when attached to adjacent carbon atoms, together represent methylenedioxy;

X and Y independently represent hydrogen, halogen, $C_{1-6}$ alkyl, $C_{1-6}$ alkoxy or phenyl; and $R^1$ represents $C_{1-6}$ alkyl or an optionally substituted aryl($C_{1-6}$)alkyl group.

The present invention also provides a compound of formula I as depicted above, or a salt thereof, wherein A and B independently represent hydrogen, halogen, cyano, nitro, trifluoromethyl, trifluoromethoxy, $C_{1-6}$ alkyl or $C_{1-6}$ alkoxy; and X, Y and $R^1$ are as defined above.

Where $R^1$ represents aryl($C_{1-6}$)alkyl, this group may be optionally substituted by one or more substituents. Suitably, the aryl($C_{1-6}$)alkyl group $R^1$ is unsubstituted, or substituted by one, two or three substituents. More particularly, the aryl($C_{1-6}$)alkyl group $R^1$ may be unsubstituted, or substituted by one or two substituents. In general, the aryl($C_{1-6}$) alkyl group $R^1$ may be unsubstituted or monosubstituted. Any optional substitution on the aryl($C_{1-6}$)alkyl group $R^1$ will suitably be on the aryl moiety thereof, although substitution on the alkyl moiety thereof is an alternative possibility. Examples of optional substituents on the group $R^1$ include halogen, nitro, trifluoromethyl, $C_{1-6}$ alkyl, hydroxy, $C_{1-6}$ alkoxy, $C_{1-6}$ alkylthio or di($C_{1-6}$)alkylamino.

In an alternative embodiment, the group $R^1$ may be optionally substituted by one or more substituents selected from halogen, cyano, trifluoromethyl, hydroxy, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di($C_{1-6}$)alkylamino, di($C_{1-6}$)alkylaminomethyl, $C_{2-6}$ alkylcarbonylamino, arylcarbonylamino, $C_{2-6}$ alkoxycarbonylamino, N-($C_{1-6}$)alkyl-N-($C_{2-6}$)alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$)alkylaminocarbonylamino, mono- or diarylaminocarbonylamino, pyrrolidinylcarbonylamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$) alkylaminosulphonyl, aminosulphonylmethyl, $C_{1-6}$ alkylaminosulphonylmethyl and di($C_{1-6}$) alkylaminosulphonylmethyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy", "$C_{1-6}$ alkylthio" and "$C_{1-6}$ alkylamino" are to be construed accordingly.

Typical aryl groups include phenyl and naphthyl, preferably phenyl.

The expression "aryl($C_{1-6}$)alkyl" as used herein includes benzyl, phenylethyl, phenylpropyl, naphthylmethyl and naphthylethyl, especially phenylethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Particular values for the substituent A in the compounds of formula I above include hydrogen, fluoro, trifluoromethyl, methyl and methoxy, especially hydrogen. More particularly, A may represent hydrogen or fluoro, especially hydrogen.

Suitably, B represents hydrogen, fluoro, chloro, cyano, nitro, trifluoromethyl, trifluoromethoxy or amino. In an alternative embodiment, B may represent hydrogen, fluoro, chloro, cyano, nitro, trifluoromethyl, trifluoromethoxy, methyl or methoxy, especially hydrogen.

In addition, A and B, when attached to adjacent carbon atoms, may together represent methylenedioxy.

Particular values for the substituent X include hydrogen, fluoro and methoxy, especially hydrogen.

Suitably, Y represents hydrogen, fluoro, chloro, bromo, methyl, methoxy or phenyl, especially hydrogen. More particularly, Y may represent hydrogen, fluoro or chloro, especially hydrogen.

Suitably, $R^1$ represents methyl, ethyl, optionally substituted benzyl, optionally substituted phenylethyl or optionally substituted phenylpropyl. In addition, $R^1$ may represent optionally substituted naphthylethyl.

Preferably, $R^1$ represents phenylethyl, which may be unsubstituted, or substituted by one or more substituents. Typically, the phenylethyl group $R^1$ will be unsubstituted, or substituted by one, two or three (especially one or two) substituents. More preferably, $R^1$ represents unsubstituted or monosubstituted phenylethyl.

Examples of specific substituents on the group $R^1$ include fluoro, chloro, bromo, iodo, nitro, trifluoromethyl, methyl, hydroxy, methoxy, methylthio and dimethylamino.

Alternatively, typical substituents on the group $R^1$ include fluoro, chloro, cyano, methoxy, amino, methylamino, dimethylamino, dimethylaminomethyl, acetylamino, methoxycarbonylamino, tert-butoxycarbonylamino, N-methoxycarbonyl-N-methylamino, methylsulphonylamino, aminocarbonylamino, aminocarbonyl, methylaminocarbonyl, dimethylaminocarbonyl, aminosulphonyl and methylaminosulphonylmethyl.

Representative values of $R^1$ include methyl, ethyl, benzyl, fluorobenzyl, cyanobenzyl, methoxybenzyl, aminobenzyl, dimethylaminomethyl-benzyl, acetylamino-benzyl, aminocarbonyl-benzyl, methylaminocarbonyl-benzyl, dimethylaminocarbonyl-benzyl, aminosulphonyl-benzyl, phenylethyl, fluoro-phenylethyl, cyano-phenylethyl, amino-phenylethyl, dimethylamino-phenylethyl, acetylamino-phenylethyl, methoxycarbonylamino-phenylethyl, (N-methoxycarbonyl-N-methyl)amino-phenylethyl, aminocarbonylamino-phenylethyl and phenylpropyl (especially 2-phenylpropyl).

Particular values of $R^1$ include methyl, benzyl and phenylethyl. A more particular value of $R^1$ is 2-phenylethyl.

Specific values of $R^1$ include phenylethyl, fluoro-phenylethyl, chloro-phenylethyl, bromo-phenylethyl, iodo-phenylethyl, difluoro-phenylethyl, dichloro-phenylethyl, (chloro)(fluoro)-phenylethyl, (fluoro)-(trifluoromethyl)-phenylethyl, (bromo)(methoxy)-phenylethyl, trifluoro-phenylethyl, nitro-phenylethyl, methyl-phenylethyl, hydroxy-phenylethyl, methoxy-phenylethyl, dimethoxy-phenylethyl, (hydroxy)(methoxy)-phenylethyl, (hydroxy)(dimethoxy)-phenylethyl, trimethoxy-phenylethyl, methylthio-phenylethyl, dimethylamino-phenylethyl, phenylpropyl, hydroxy-phenylpropyl and naphthylethyl.

A particular sub-class of compounds according to the invention is represented by the compounds of formula II, and salts thereof:

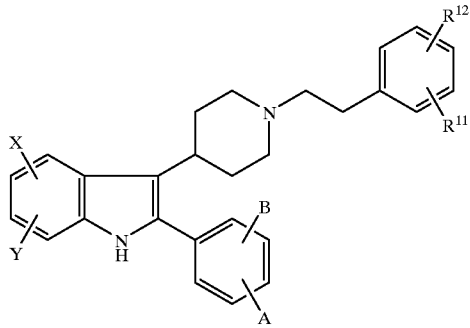

(II)

wherein

A, B, X and Y are as defined with reference to formula I above; and $R^{11}$ and $R^{12}$ independently represent hydrogen, halogen, nitro, trifluoromethyl, $C_{1-6}$ alkyl, hydroxy, $C_{1-6}$ alkoxy, $C_{1-6}$ alkylthio or di($C_{1-6}$)alkylamino.

The present invention also provides a compound of formula II as depicted above, or a salt thereof wherein $R^{11}$ and $R^{12}$ independently represent hydrogen, halogen, $C_{1-6}$ alkyl or $C_{1-6}$ alkoxy; and A, B, X and Y are as defined above.

Suitably, $R^{11}$ represents hydrogen, fluoro, chloro or methoxy, especially hydrogen. More particularly, $R^{11}$ may represent hydrogen or fluoro, especially hydrogen.

Suitably, $R^{12}$ represents hydrogen, fluoro, chloro, bromo, iodo, nitro, trifluoromethyl, methyl, hydroxy, methoxy, methylthio or dimethylamino. More particularly, $R^{12}$ may represent hydrogen, fluoro, chloro, methyl or methoxy, especially hydrogen.

Specific compounds within the scope of the present invention include:

3-(1-methylpiperidin-4-yl)-2-phenyl-1H-indole;

3-(1-benzylpiperidin-4-yl)-2-phenyl-1H-indole;

2-phenyl-3-[1-(2-phenylethyl)piperidin-4-yl]-1H-indole;

5-chloro-3-[1-(2-phenylethyl)piperidin-4-yl]-2-phenyl-1H-indole;

3-[1-(2-phenylethyl)piperidin-4-yl]-2-(3-fluorophenyl)-1H-indole;

3-[1-(2-phenylethyl)piperidin-4-yl]-2-(2-fluorophenyl)-1H-indole;

3-[1-(2-phenylethyl)piperidin-4-yl]-2-(2,3-difluorophenyl)-1H-indole;

3-[1-(2-phenylethyl)piperidin-4-yl]-2-(3,4-difluorophenyl)-1H-indole;

3-[1-(2-phenylethyl)piperidin-4-yl]-2-(2,4-difluorophenyl)-1H-indole;

3-[1-(2-phenylethyl)piperidin-4-yl]-2-(4-fluorophenyl)-1H-indole;

3-[1-(2-phenylethyl)piperidin-4-yl]-2-(3,5-difluorophenyl)-1H-indole;

3-[1-(2-phenylethyl)piperidin-4-yl]-2-(2,5-difluorophenyl)-1H-indole;

3-[1-(2-phenylethyl)piperidin-4-yl]-2-(3-chlorophenyl)-1H-indole;

3-[1-(2-phenylethyl)piperidin-4-yl]-2-(3-nitrophenyl)-1H-indole;

3-[1-(2-phenylethyl)piperidin-4-yl]-2-(3-trifluoromethylphenyl)-1H-indole;

3-[1-(2-phenylethyl)piperidin-4-yl]-2-(3,4-methylenedioxyphenyl)-1H-indole;

3-[1-(2-phenylethyl)piperidin-4-yl]-2-(3-cyanophenyl)-1H-indole;

3-[1-(2-phenylethyl)piperidin-4-yl]-2-(3-trifluoromethoxyphenyl)-1H-indole;

3-[1-(2-phenylethyl)piperidin-4-yl]-2-(3-aminophenyl)-1H-indole;

3-[1-(2-(2-fluorophenyl)ethyl)piperidin-4-yl]-2-phenyl-1H-indole;

3-[1-(2-(3-fluorophenyl)ethyl)piperidin-4-yl]-2-phenyl-1H-indole;

3-[1-(2-(4-fluorophenyl)ethyl)piperidin-4-yl]-2-phenyl-1H-indole;

3-[1-(1-hydroxy-3-phenylprop-2-yl)piperidin-4-yl]-2-phenyl-1H-indole;

6-chloro-3-[1-(2-phenylethyl)piperidin-4-yl]-2-phenyl-1H-indole;

6-fluoro-3-[1-(2-phenylethyl)piperidin-4-yl]-2-phenyl-1H-indole;

4-fluoro-3-[1-(2-phenylethyl)piperidin-4-yl]-2-phenyl-1H-indole;

7-fluoro-3-[1-(2-phenylethyl)piperidin-4-yl]-2-phenyl-1H-indole;

3-[1-(2-(2,3,5-trifluorophenyl)ethyl)piperidin-4-yl]-2-phenyl-1H-indole;

3-[1-(2-(2-hydroxyphenyl)ethyl)piperidin-4-yl]-2-phenyl-1H-indole;

3-[1-(2-(3-hydroxyphenyl)ethyl)piperidin-4-yl]-2-phenyl-1H-indole;

3-[1-(2-(3-nitrophenyl)ethyl)piperidin-4-yl]-2-phenyl-1H-indole;

3-[1-(2-(4-dimthylamnophenyl)ethyl)piperidin-4-yl]-2-phenyl-1H-indole;

3-[1-(2-(4-methylthiophenyl)ethyl)piperidin-4-yl]-2-phenyl-1H-indole;

3-[1-(2-(3-methoxyphenyl)ethyl)piperidin-4-yl]-2-phenyl-1H-indole;

3-[1-(2-(naphth-1-yl)ethyl)piperidin-4-yl -2-phenyl-1H-indole;

3-[1-(2-(4-bromophenyl)ethyl)piperidin-4-yl]-2-phenyl-1H-indole;

3-[1-(2-(3,4-dichorophenyl)ethyl)piperidin4-yl]-2-phenyl-1H-indole;

3-[1-(2-(2-chloro-4-fluorophenyl)ethyl)piperidin-4-yl]-2-phenyl-1H-indole;

3-[1-(2-(3,4-dimethoxrphenyl)ethyl)piperidin-4yl]-2-phenyl-1H-indole;

3-[1-(2-(3,4,5-trmethoxyphenyl)ethyl)piperldin-4-yl]-2-phenyl-1H-indole;

3-[1-2-(3-methphenyl)ethyl)pperldin-4-yl]-2-phenyl-1H-indole;

3-[1-(2-(2,4-dichlorophenyl)ethyl)piperidin-4-yl]-2-phenyl-1H-indole;

3-[1-(2-(2,4-difluorophenyl)ethyl)piperidin-4-yl]-2-phenyl-1H-indole;

3-[1-(2-(5-bromo-2-methoxyphenyl)ethyl)piperidin-4-yl]-2-phenyl-1H-indole;

3-[1-(2-(2-fluoro-4-trifluoromethylphenyl)ethyl)piperidin-4-yl]-2-phenyl-1H-indole;

3-[1-(2-(3-chlorophenyl)ethyl)piperidin-4-yl]-2-phenyl-1H-indole;

3-[1-(2-(4-iodophenyl)ethyl)piperidin-4-yl]-2-phenyl-1H-indole;

3-[1-(2-(3-bromophenyl)ethyl)piperidin-4-yl]-2-phenyl-1H-indole;

3-[1-(2-(4-nitrophenyl)ethyl)piperidin-4-yl]-2-phenyl-1H-indole;

3-[1-(2-(4-hydroxy-3,5-dimethoxyphenyl)ethyl)piperidin-4-yl]-2-phenyl-1H-indole;

3-[1-(2-(4-hydroxyphenyl)ethyl)piperidin-4-yl]-2-phenyl-1H-indole;

3-[1-(2-(4-hydroxy-3-methoxyphenyl)ethyl)piperidin-4-yl]-2-phenyl-1H-indole;

3-[1-(3-hydroxy-3-phenylpropyl)piperidin-4-yl]-2-phenyl-1H-indole;

3-[1-(2-(3,4-difluorophenyl)ethyl)piperidin-4-yl]-2-phenyl-1H-indole;

3-[1-(2-(2-chlorophenyl)ethyl)piperidin-4-yl]-2-phenyl-1H-indole;

3-[2-(2-bromophenyl)ethyl)piperidin-4-yl]-2-phenyl-1H-indole;

3-[1-(2-fluoro-2-phenylethyl)piperidin-4-yl]-2-phenyl-1H-indole;

3-[1-(2-(4-chlorophenyl)ethyl)piperidin-4-yl]-2-phenyl-1H-indole;

3-[1-(3-phenylpropyl)pieperidin-4-yl]-2-phenyl-1H-indole;

6-fluoro-3-[1-(2-phenylethyl)piperidin-4-yl]-2-(2-fluorophenyl)-1H-indole;

5-fluoro-3-[1-(2-phenylethyl)piperidin-4-yl]-2-phenyl-1H-indole; and salts thereof.

The invention also provides pharmaceutical compositions comprising one or more of the compounds according to this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

If desired, the compounds according to this invention may be co-administered with another anti-schizophrenic medicament, for example one producing its effects via dopamine $D_2$ and/or $D_4$ receptor subtype blockade. In such circumstances, an enhanced anti-schizophrenic effect may be envisaged without a corresponding increase in side-effects such as those caused by, for example, $D_2$ receptor subtype blockade; or a comparable anti-schizophrenic effect with reduced side-effects may alternatively be envisaged. Such co-administration may be desirable where a patient is already established on an anti-schizophrenic treatment regime involving conventional anti-schizophrenic medicaments. Suitable anti-schizophrenic medicaments of use in combination with the compounds according to the present invention include haloperidol, chlorpromazine, mesoridazine, thioridazine, acetophenazine, fluphenazine, perphenazine, trifluoperazine, chloroprothixene, thiothixene, clozapine, olanzapine, pimozide, molindone, loxapine, sulpiride, risperidone, xanomeline, fananserin and ziprasidone, and pharmaceutically acceptable salts thereof.

The compounds according to the present invention may be prepared by a process which comprises attachment of the $R^1$ moiety to a compound of formula III:

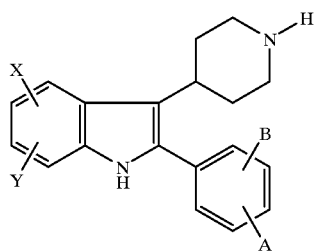

(III)

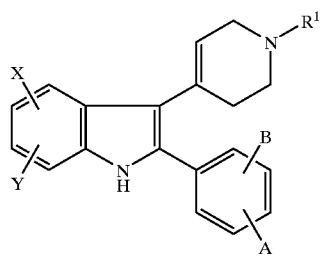

(V)

wherein A, B, X and Y are as defined above; by conventional means including N-alkylation.

Attachment of the $R^1$ moiety to the compounds of formula III may conveniently be effected by standard alkylation techniques. One example thereof comprises treatment with an alkyl halide such as methyl iodide, or an aryl($C_{1-6}$)alkyl halide such as benzyl bromide or 2-phenylethyl bromide, typically under basic conditions, e.g. potassium carbonate or caesium carbonate in N,N-dimethylformamide. Another example comprises treatment of the compound of formula III with an aryl($C_{1-6}$)alkyl mesylate such as 2-phenylethyl methanesulphonate, typically in the presence of sodium carbonate and sodium iodide, in a suitable solvent such as 1,2-dimethoxyethane.

Alternatively, the $R^1$ moiety may conveniently be attached by reductive alkylation, which may be accomplished in a single step, or as a two-step procedure. The single-step approach suitably comprises treating the required compound of formula III as defined above with the appropriate aldehyde, e.g. formaldehyde, benzaldehyde or phenylacetaldehyde, in the presence of a reducing agent such as sodium cyanoborohydride. In a typical two-step procedure, for the preparation of a compound of formula I wherein $R^1$ corresponds to a group of formula —$CH_2R^{1a}$, a carboxylic acid derivative of formula $R^{1a}$—$CO_2H$ is condensed with the required compound of formula III, suitably in the presence of 1-(3-dimethylaminopropyl)-3-ethylcarbodiimide hydrochloride and 1-hydroxybenzotriazole hydrate, to afford a compound corresponding to formula I wherein $R^1$ represents —$COR^{1a}$; the carbonyl group thereof can then be reduced, for example by treatment with diisobutylaluminium hydride, and the required compound of formula I thereby obtained.

The compounds of formula III above may be prepared by reduction of the corresponding compound of formula IV:

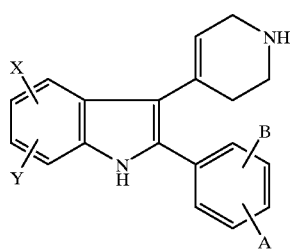

(IV)

wherein A, B, X and Y are as defined above.

Similarly, the compounds according to the invention may be prepared by a process which comprises reducing a compound of formula V:

wherein A, B, X, Y and $R^1$ are as defined above.

Reduction of the compounds of formula IV or V may conveniently be accomplished by conventional catalytic hydrogenation, which comprises treating the appropriate compound with hydrogen in the presence of a hydrogenation catalyst such as palladium on charcoal. Alternatively, compound IV or V may be reduced by transfer hydrogenation using a hydrogenation catalyst such as palladium on charcoal in the presence of a hydrogen donor such as ammonium formate, typically in a lower alkanol solvent such as methanol.

The intermediates of formula IV and V may be prepared by reacting a compound of formula VI with the appropriate piperidinone derivative of formula VII:

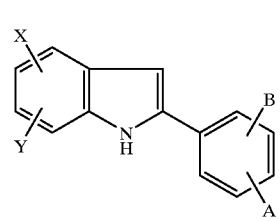

(VI)

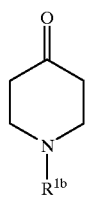

(VII)

wherein A, B, X and Y are as defined above, and Rib represents hydrogen or corresponds to the moiety $R^1$ as defined above.

The reaction between compounds VI and VII is conveniently effected by heating the reactants under acidic conditions, typically in a mixture of phosphoric acid and acetic acid at a temperature in the region of 80° C.

The intermediates of formula III and of formula V above are novel compounds in their own right, and represent further features of the present invention.

In another procedure, the compounds according to the invention may be prepared by a process which comprises reacting a compound of formula VIII or an acid addition salt thereof, typically the hydrochloride salt, with a compound of formula IX:

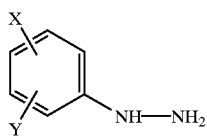

(VIII)

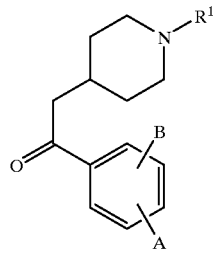

(IX)

wherein A, B, X, Y and $R^1$ are as defined above.

The reaction between compounds VIII and IX, which is an example of the well-known Fischer indole synthesis, is suitably effected by stirring in ethanol at 25° C., followed by heating in trifluoroacetic acid at 70° C.

In a further procedure, the compounds according to the invention may be prepared by a process which comprises reacting a compound of formula X with a compound of formula XI (cf. Larock and Yum, *J. Am. Chem. Soc.*, 991, 113, 6689):

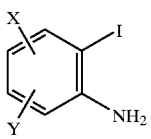

(X)

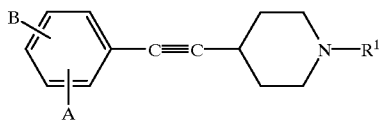

(XI)

wherein A, B, X, Y and $R^1$ are as defined above; in the presence of a transition metal catalyst.

The transition metal catalyst employed in the reaction between compounds X and XI is suitably a palladium-containing catalyst. Typical catalysts include palladium(II) acetate, optionally in the presence of triphenylphosphine, and dichlorobis(triphenylphosphine)palladium(II). A preferred catalyst is dichlorobis(triphenylphosphine)palladium (II).

The transition metal catalysed indole formation reaction between compounds X and XI is advantageously carried out under basic conditions. Typical basic reagents of use in the reaction include sodium carbonate, potassium carbonate, sodium acetate or potassium acetate, optionally in the presence of lithium chloride or tetra-n-butylammonium chloride; and tetramethylguanidine. A preferred base is tetramethylguanidine. The reaction is conveniently effected in a polar aprotic organic solvent such as N,N-dimethylformamide, typically at an elevated temperature, e.g. a temperature in the region of 80–110° C.

Where they are not commercially available, the starting materials of formula VI, VII, VIII, IX, X and XI may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds of use in the invention.

The compounds in accordance with this invention potently inhibit [$^3$H]-ketanserin binding to the human 5-HT$_{2A}$ receptor expressed in clonal cell lines. Moreover, those compounds of the invention which have been tested display a selective affinity for the 5-HT$_{2A}$ receptor relative to the dopamine D$_2$ receptor.

The compounds of the accompanying Examples were all found to possess a K$_i$ value for displacement of [$^3$H]-ketanserin from the human 5-HT$_{2A}$ receptor, when expressed in Chinese hamster ovary (CHO) clonal cell lines, of 100 nM or less.

EXAMPLE 1

3-(1-Methylpiperidin-4-yl)-2-Phenyl-1H-indole

Step 1: 3-(1,2,3,6-Tetrahydropyridin-4-yl)-2-phenyl-1H-indole

2-Phenylindole (25 g, 130 mmol) was stirred at 80° C. in AcOH (200 ml), and 4-piperidone hydrochloride hydrate (50 g, 376 mmol) and 1M phosphoric acid (100 ml) added. After a further 6 h, the mixture was poured into ice/ammonia, and extracted with EtOAc (3×200 ml). The combined organic layers were washed with water and brine, dried, and evaporated in vacuo to give a pale yellow solid. This was suspended in boiling EtOAc (200 ml), cooled to room temperature overnight, and the solid collected, washed with EtOAc and dried to give the title compound (26 g, 73%) as a pale yellow solid; $\delta_H$ (360 MHz, d$_6$-DMSO) 2.00–2.10 (2H, m, NCH$_2$CH$_2$), 2.89 (2H, t, J 5, NCH$_2$CH$_2$), 3.40–3.45 (2H, m, NCH$_2$CH), 5.78 (1H, br s, NCH$_2$CH), 7.00 (1H, t, J 7, indole-H), 7.08 (1H, t, J 7, indole-H), 7.20–7.50 (5H, m, ArH), 7.69 (2H, d, J 7, ArH), 11.3 (1H, br s, indole NH); m/z (ES$^+$) 275 (M$^+$+H).

Step 2: 3-(Piperidin-4-yl)-2-phenyl-1H-indole 3-(1,2,3,6-Tetrahydropyridin-4-yl)-2-phenyl-1H-indole (25 g, 91 mmol), palladium on carbon (10% w/w, 2.5 g) and NH₄HCO₂ (57 g, 0.72 mol) were refluxed in MeOH (300 ml) for 8 h. Palladium on carbon (10% w/w, 1.25 g) and NH₄HCO₂ (29 g, 0.36 mol) were added, and refluxing continued for 8 h. The mixture was cooled, filtered, and evaporated to give a white solid. This was suspended in H₂O (1 l) and 1M NaOH (100 ml), and the mixture extracted with CH₂Cl₂ (5×150 ml). The combined organic layers were washed with water and brine, dried, and evaporated in vacuo to give a white solid, which was recrystallised from MeOH (300 ml) and H₂O (100 ml) to give the title compound (19 g, 75%) as white crystals, mp 187–188° C. Oxalate salt, white crystals, mp 209–211° C. (from EtOH). Found C, 69.09; H, 6.65; N, 7.52. $C_{19}H_{20}N_2 \cdot C_2H_2O_4$ requires C, 68.84; H, 6.05; N, 7.65%; $\delta_H$ (360 MHz, d₆-DMSO) 1.80 (2H, d, J 13, NCH₂CH$_A$H$_B$), 2.30–2.50 (2H, m, NCH₂CH$_A$H$_B$), 2.91 (2H, t, J 12, NCH$_A$H$_B$), 3.10–3.20 (1H, m, CH₂CH), 3.32 (2H, d, J 12, NCH$_A$H$_B$), 6.98 (1H, t, J 7, indole-H), 7.08 (1H, t, J 7, indole-H), 7.20–7.50 (6H, m, ArH), 7.88 (1H, d, J 7, ArH), 11.3 (1H, br s, indole NH); m/z (ES⁺) 277 (M⁺+H).

Step 3: 3-(1-Methylpiperidin-4-yl)-2-phenyl-1H-indole 3-(Piperidin-4-yl)-2-phenyl-1H-indole (200 mg, 0.7 mmol), sodium cyanoborohydride (51 mg, 0.8 mmol), formaldehyde (60 μl, 40% in H₂O, 0.8 mmol) and AcOH (97 μl, 1.7 mmol) were stirred in MeOH (5 ml) at 0° C. for 1 h, then room temperature for 2 h. The solution was poured into saturated NaHCO₃ solution and extracted with EtOAc. The organic layer was washed with water and brine, dried, and evaporated in vacuo to give white crystals (49 mg, 23%), mp 245–246° C. (from EtOH); $\delta_H$ (360 MHz, d₆-DMSO) 1.88 (2H, d, J 13, NCH₂CH$_A$H$_B$), 2.60–2.80 (2H, m, NCH₂CH$_A$H$_B$), 2.76 (3H, s, CH₃), 3.00–3.20 (3H, m, CH₂CH and NCH$_A$H$_B$), 3.44 (2H, d, J 12, NCH$_A$H$_B$), 6.99 (1H, t, J 7, indole-H), 7.09 (1H, t, J 7, indole-H), 7.20–7.50 (6H, m, ArH), 7.98 (1H, d, J 7, ArH), 11.20 (1H, br s, indole NH); m/z (ES⁺) 291 (M⁺+H).

EXAMPLE 2

3-(1-Benzylpiperidin-4-yl)-2-phenyl-1H-indole 3-(Piperidin-4-yl)-2-phenyl-1H-indole (150 mg, 0.54 mmol), benzyl bromide (80 μl, 0.66 mmol), and K₂CO₃ (0.15 g, 1.08 mmol) were stirred in DMF (3 ml) at room temperature overnight. The mixture was poured into water and extracted with EtOAc. The organic layer was washed with water and brine, dried, evaporated in vacuo and purified by flash chromatography eluting with CH₂Cl₂:MeOH (93:7 v/v) to give the product as a solid (129 mg, 65%): oxalate salt, white crystals, mp 160–164° C. (dec.) (from MeOH). Found C, 70.87; H, 6.13; N, 5.93. $C_{26}H_{26}N_2 \cdot C_2H_2O_4 \cdot H_2O$ requires C, 70.87; H, 6.37; N, 5.90%; $\delta_H$ (360 MHz, d₆-DMSO) 2.00 (2H, d, J 13, NCH₂CH$_A$H$_B$), 2.60–2.80 (2H, m, NCH₂CH$_A$H$_B$), 3.00–3.10 (2H, m, NCH$_A$H$_B$), 3.20–3.30 (1H, m, CH₂CH), 3.50–3.60 (2H, m, NCH$_A$H$_B$), 4.39 (2H, s, PhCH₂), 7.12 (1H, t, J 7, indole-H), 7.23 (1H, t, J 7, indole-H), 7.50–7.70 (11H, m, ArH), 8.00 (1H, d, J8, ArH), 11.20 (1H, br s, indole NH); m/z (ES⁺) 367 (M⁺+H).

EXAMPLE 3

2-Phenyl-3-[1-(2-phenylethyl)piperidin-4-yl]-1H-indole 3-(Piperidin-4-yl)-2-phenyl-1H-indole (150 mg, 0.54 mmol), phenethyl bromide (90 μl, 0.64 mmol), and K₂CO₃ (0.15 g, 1.08 mmol) were stirred in DMF (3 ml) at room temperature overnight. The mixture was poured into water and extracted with EtOAc. The organic layer was washed with water and brine, dried, evaporated in vacuo and purified by flash chromatography eluting with CH₂Cl₂:MeOH (93:7 v/v) to give the product (189 mg, 91 %): oxalate salt, white crystals, mp 209–211° C. (dec.) (from MeOH/Et₂O). Found C, 71.43; H, 6.44; N, 6.02. $C_{27}H_{28}N_2 \cdot C_2H_2O_4 \cdot H_2O$ requires C, 71.29; H, 6.60; N, 5.73%; $\delta_H$ (360 MHz, d₆-DMSO) 1.92 (2H, d, J 13, NCH₂CH$_A$H$_B$), 2.50–2.70 (2H, m, NCH₂CH$_A$H$_B$), 2.90–3.10 (4H, m, CH₂), 3.10–3.20 (1H, m, CH₂CH), 3.20–3.30 (2H, m, CH₂), 3.60 (2H, d, J 12, NCH$_A$H$_B$), 7.00 (1H, t, J 7, indole-H), 7.10 (1H, t, J 7, indole-H), 7.50–7.70 (11H, m, ArH), 7.88 (1H, d, J 8, ArH), 11.20 (1H, br s, indole NH); m/z (ES⁺) 381 (M⁺+H).

EXAMPLES 4 To 61

The following compounds were prepared by methods analogous to those decribed above.

Example 4: 5-Chloro-3-[1-(2-phenylethyl)piperidin-4-yl]-2-phenyl-1H-indole

Example 5: 3-[1-(2-Phenylethyl)piperidin-4-yl]-2-(3-fluorophenyl)-1H-indole

Example 6: 3-[1-(2-Phenylethyl)piperidin-4-yl]-2-(2-fluorophenyl)-1H-indole

Example 7: 3-[1-(2-Phenylethyl)piperidin-4-yl]-2-(2,3-difluorophenyl)-1H-indole

Example 8: 3-[1-(2-Phenylethyl)piperidin-4-yl]-2-(3,4-difluorophenyl)-1H-indole

Example 9: 3-[1-(2-Phenylethyl)piperidin-4-yl]-2-(2,4-difluorophenyl)-1H-indole

Example 10: 3-[1-(2-Phenylethyl)piperidin-4-yl]-2-(4-fluorophenyl)-1H-indole

Example 11: 3-[1-(2-Phenylethyl)piperldin-4-yl]-2-(3,5-difluorophenyl)-1H-indole Example 12: 3-[1-(2-Phenylethyl)piperidin-4-yl]-2-(2,5-difluorophenyl)-1H-indole Example 13: 3-[1-(2-Phenylethyl)piperidin-4-yl]-2-(3-chlorophenyl)-1H-indole Example 14: 3-[1-(2-Phenylethyl)piperidin-4-yl]-2-(3-nitrophenyl)-1H-indole Example 15: 3-[1-(2-Phenylethyl)piperidin-4-yl]-2-(3-trifluoromethyl-phenyl)-1H-indole Example 16: 3-[1-(2-Phenylethyl)piperidin-4-yl]-2-(3,4-methylenedioxy-phenyl)-1H-indole Example 17: 3-[1-(2-Phenylethyl)piperidin-4-yl]-2-(3-cyanophenyl)-1H-indole Example 18: 3-[1-(2-Phenylethyl)piperidin-4-yl]-2-(3-trifluoromethoxy-phenyl)-1H-indole Example 19: 3-[1-(2-Phenylethyl)piperidin-4-yl]-2-(3-aminophenyl)-1H-indole Example 20: 3-[1-(2-(2-Fluorophenyl)ethyl)piperidin-4-yl]-2-phenyl-1H-indole Example 21: 3-[1-(2-(3-Fluorophenyl)ethyl)piperidin-4-yl]-2-phenyl-1H-indole Example 22: 3-[1-(2-(4-Fluorophenyl)ethyl)piperidin-4-yl]-2-phenyl-1H-indole Example 23: 3-[1-(1-Hydroxy-3-phenylprop-2-yl)piperidin-4-yl]-2-phenyl-1H-indole Example 24: 6-Chloro-3-[1-(2-phenylethyl)piperidin-4-yl]-2-phenyl-1H-indole Example 25: 6-Fluoro-3-[1-(2-phenylethyl)piperidin-4-yl]-2-phenyl-1H-indole Example 26: 4-Fluoro-3-[1-(2-phenylethyl)piperidin-4-yl]-2-phenyl-1H-indole Example 27: 7-Fluoro-3-[1-(2-phenylethyl)piperidin-4-yl]-2-phenyl-1H-indole
Example 28: 3-[1-(2-(2,3,5-Trifluorophenyl)ethyl)piperidin-4-yl]-2-phenyl-1H-indole
Example 29: 3-[1-(2-(2-Hydroxyphenyl)ethyl)piperidin-4-yl]-2-phenyl-1H-indole
Example 30: 3-[1-(2-(3-Hydroxyphenyl)ethyl)piperldin-4-yl]-2-phenyl-1H-indole
Example 31: 3-[1-(2-(3-Nitrophenyl)ethyl)piperidin-4-yl]-2-phenyl-1H-indole
Example 32: 3-[1-(2-(4-Dimethylaminophenyl)ethyl)piperidin-4-yl]-2-phenyl-1H-indole
Example 33: 3-[1-(2-(4-Methylthiophenyl)ethyl)piperidin-4-yl]-2-phenyl-1H-indole
Example 34: 3-[1-(2-(3-Methoxyphenyl)ethyl)piperidin-4-yl]-2-phenyl-1H-indole
Example 35: 3-[1-(2-(Naphth-1-yl)ethyl)piperidin-4-yl]-2-phenyl-1H-indole
Example 36: 3-[1-(2-(4-Bromophenyl)ethyl)piperidin-4-yl]-2-phenyl-1H-indole
Example 37: 3-[1-(2-(3,4-Dichlorophenyl)ethyl)piperidin-4-yl]-2-phenyl-1H-indole
Example 38: 3-[1-(2-(2-Chloro-4-fluorophenyl)ethyl)piperidin-4-yl]-2-phenyl-1H-indole
Example 39: 3-[1-(2-(3, 4-Dimethoxyphenyl)ethyl)piperidin-4-yl]-2-phenyl-1H-indole
Example 40: 3-[1-(2-(3,4, 5-Trimethoxyphenyl)ethyl)piperidin-4-yl]-2-phenyl-1H-indole
Example 41: 3-[-(2-(3-Methylphenyl)ethyl)piperidin-4-yl]-2-phenyl-1H-indole
Example 42: 3-[1-(2-(2,4-Dichlorophenyl)ethyl)piperidin-4-yl]-2-phenyl-1H-indole
Example 43: 3-[1-(2-(2,4-Difluorophenyl)ethyl)piperidin-4-yl]-2-phenyl-1H-indole
Example 44: 3-[1-(2-(5-Bromo-2-methoxyphenyl)ethyl)piperldin-4-yl]-2-phenyl-1H-indole
Example 45: 3-[1-(2-(2-Fluoro-4-trifluoromethylphenyl)ethyl)piperidin-4-yl]-2-phenyl-1H-indole
Example 46: 3-[1-(2-(3-Chlorophenyl)ethyl)piperidin-4-yl]-2-phenyl-1H-indole
Example 47: 3-[1-(2-(4-Iodophenyl)ethyl)piperidin-4-yl]-2-phenyl-1H-indole
Example 48: 3-[1-(2-(3-Bromophenyl)ethyl)piperidin-4-yl]-2-phenyl-1H-indole
Example 49: 3-[1-(2-(4-Nitrophenyl)ethyl)piperldin-4-yl]-2-phenyl-1H-indole
Example 50: 3-[1-(2-(4-Hydroxy-3,5-dimethoxyphenyl)ethyl)piperidin-4-yl]-2-phenyl-1H-indole
Example 51: 3-[1-(2-(4-Hydroxyphenyl)ethyl)piperldin-4-yl]-2-phenyl-1H-indole
Example 52: 3-[1-(2-(4-Hydroxy-3-methoxyphenyl)ethyl)piperldin-4-yl]-2-phenyl-1H-indole
Example 53: 3-[1-(3-Hydroxy-3-phenylpropyl)piperidin-4-yl]-2-phenyl-1H-indole
Example 54: 3-[1-(2-(3,4-Difluorophenyl)ethyl)piperidin-4-yl]-2-phenyl-1H-indole
Example 55: 3-[1-(2-(2-chlorophenyl)ethyl)piperidin-4-yl]-2-phenyl-1H-indole Example 56: 3-[1-(2-(2-bromophenyl)ethyl)piperidin-4-yl]-2-phenyl-1H-indole Example 57: 3-[1-(2-fluoro-2-phenylethyl)piperidin-4-yl]-2-phenyl-1H-indole Example 58: 3-[1-(2-(4-chlorophenyl)ethyl)piperidin-4-yl]-2-phenyl-1H-indole Example 59: 3-[1-(3-phenylpropyl)piperidin-4-yl]-2-phenyl-1H-indole Example 60: 6-fluoro-3-[1-(2-phenylethyl)piperidin-4-yl]-2-(2-fluorophenyl)-1H-indole Example 61: 5-fluoro-3-[1-(2-phenylethyl)piperidin-4-yl]-2-phenyl-1H-indole

What is claimed is:

1. A compound of formula I, or a pharmaceutically acceptable salt thereof:

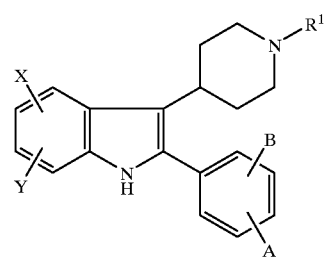

(I)

wherein

A and B independently represent hydrogen, halogen, cyano, nitro, trifluoromethyl, trifluoromethoxy, $C_{1-6}$ alkyl, $C_{1-6}$ alkoxy or amino; or A and B, when attached to adjacent carbon atoms, together may represent methylenedioxy;

X and Y independently represent hydrogen, halogen, $C_{1-6}$ alkyl, $C_{1-6}$ alkoxy or phenyl; and $R^1$ represents an optionally substituted aryl($C_{1-6}$)alkyl group, wherein aryl is selected from phenyl and naphthyl.

2. A compound as claimed in claim 1 wherein $R^1$ represents phenylethyl, either unsubstituted or substituted by one, two or three substituents selected from halogen, nitro, trifluoromethyl, $C_{1-6}$ alkyl, hydroxy, $C_{1-6}$ alkoxy, $C_{1-6}$ alkylthio or di($C_{1-6}$)alkylamino.

3. A compound as claimed in claim 2 wherein $R^1$ represents 2-phenylethyl.

4. A compound as claimed in claim 1 represented by formula II, and pharmaceutically acceptable salts and prodrugs thereof:

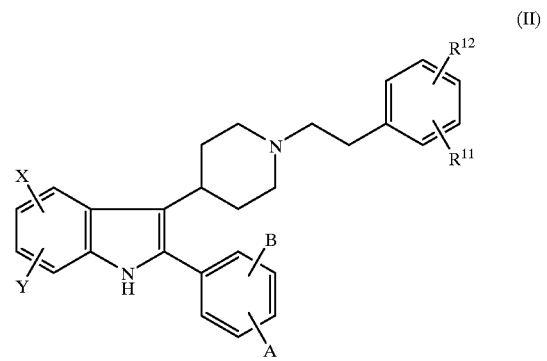

(II)

wherein

A, B, X and Y are as defined in claim 1; and $R^{11}$ and $R^{12}$ independently represent hydrogen, halogen, nitro, trifluoromethyl, $C_{1-6}$ alkyl, hydroxy, $C_{1-6}$ alkoxy, $C_{1-6}$ alkylthio or di($C_{1-6}$)alkylamino.

5. A compound selected from the group consisting of:
3-(1-benzylpiperidin-4-yl)-2-phenyl-1H-indole;
2-phenyl-3-[1-(2-phenylethyl)piperidin-4-yl]-1H-indole;
and pharmaceutically acceptable salts thereof.

6. A compound selected from the groups consisting of:
5-chloro-3-[1-(2-phenylethyl)piperidin-4-yl]-2-phenyl-1H-indole;
3-[1-(2-phenylethyl)piperidin-4-yl]-2-(3-fluorophenyl)-1H-indole;
3-[1-(2-phenylethyl)piperidin-4-yl]-2-(2-fluorophenyl)-1H-indole;
3-[1-(2-phenylethyl)piperidin-4-yl]-2-(2,3-difluorophenyl)-1H-indole;
3-[1-(2-phenylethyl)piperidin-4-yl]-2-(3,4-difluorophenyl)-1H-indole;
3-[1-(2-phenylethyl)piperidin-4-yl]-2-(2,4-difluorophenyl)-1H-indole;
3-[1-(2-phenylethyl)piperidin-4-yl]-2-(4-fluorophenyl)-1H-indole;
3-[1-(2-phenylethyl)piperidin-4-yl]-2-(3,5-difluorophenyl)-1H-indole;
3-[1-(2-phenylethyl)piperidin-4-yl]-2-(2,5-difluorophenyl)-1H-indole;
3-[1-(2-phenylethyl)piperidin-4-yl]-2-(3-chlorophenyl)-1H-indole;
3-[1-(2-phenylethyl)piperidin-4-yl]-2-(3-nitrophenyl)-1H-indole;
3-[1-(2-phenylethyl)piperidin-4-yl]-2-(3-trifluoromethylphenyl)-1H-indole;
3-[1-(2-phenylethyl)piperidin-4-yl]-2-(3,4-methylenedioxyphenyl)-1H-indole;
3-[1-(2-phenylethyl)piperidin-4-yl]-2-(3-cyanophenyl)-1H-indole;
3-[1-(2-phenylethyl)piperidin-4-yl]-2-(3-trifluoromethoxyphenyl)-1H-indole;
3-[1-(2-phenylethyl)piperidin-4-yl]-2-(3-aminophenyl)-1H-indole;
3-[1-(2-(2-fluorophenyl)ethyl)piperidin-4-yl]-2-phenyl-1H-indole;
3-[1-(2-(3-fluorophenyl)ethyl)piperidin-4-yl]-2-phenyl-1H-indole;
3-[1-(2-(4-fluorophenyl)ethyl)piperidin-4-yl]-2-phenyl-1H-indole;
3-[1-(1-hydroxy-3-phenylprop-2-yl)piperidin-4-yl]-2-phenyl-1H-indole;
6-chloro-3-[-(2-phenylethyl)piperidin-4-yl]-2-phenyl-1H-indole;
6-fluoro-3-[-(2-phenylepthyl)piperidin-4-yl]-2-phenyl-1H-indole;
4-fluoro-3-[-(2-phenylethyl)piperidin-4-yl]-2-phenyl-1H-indole;
7-fluoro-3-[1l-(2-phenylethyl)piperidin-4-yl]-2-phenyl-1H-indole;
3-[1-(2-(2,3,5-trifluorophenyl)ethyl)piperidin-4-yl]-2-phenyl-1H-indole;
3-[1-(2-(2-hydroxyphenyl)ethyl)piperidin-4-yl]-2-phenyl-1H-indole;
3-[1-(2-(3-hydroxyphenyl)ethyl)piperidin-4-yl]-2-phenyl-1H-indole;
3-[1-(2-(3-nitrophenyl)ethyl)piperidin-4-yl]-2-phenyl-1H-indole;
3-[1-(2-(4-dimethylaminophenyl)ethyl)piperidin-4-yl]-2-phenyl-1H -indole;
3-[1-(2-(4-methylthuophenyl)ethyl)piperidin-4-yl]-2-phenyl-1H-indole;
3-[1-(2-(3-methoxyphenyl)ethyl)piperidin-4-yl]-2-phenyl-1H-indole;
3-[1-(2-(naphth-1-yl)ethyl)piperidin-4-yl]-2-phenyl-1H-indole;
3-[1-(2-(4-bromophenyl)ethyl)piperidin-4-yl]-2-phenyl-1H-indole;
3-[1-(2-(3,4-dichlorophenyl)ethyl)piperidin-4-yl]-2-phenyl-1H-indole;
3-[1-(2-(2-chloro-4-fluorophenyl)ethyl)piperidin-4-yl]-2-phenyl-1H-indole;
3-[1-(2-(3,4-dimethoxyphenyl)ethyl)piperidin-4-yl]-2-phenyl-1H-indole;
3-[1-(2-(3,4,5-trimethoxyphenyl)ethyl)piperidin-4-yl]-2-phenyl-1H-indole;
3-[1-(2-(3-methylphenyl)ethyl)piperidin-4-yl]-2-phenyl-1H-indole;
3-[1-(2-(2,4-dichlorophenyl)ethyl)piperidin-4-yl]-2-phenyl-1H-indole;
3-[1-(2-(2,4-difluorophenyl)ethyl)piperidin-4-yl]-2-phenyl-1H-indole;
3-[1-(2-(5-bromo-2-methoxyphenyl)ethyl)piperidin-4-yl]-2-phenyl-1H-indole;
3-[1-(2-(2-fluoro-4-trifluoromethylphenyl)ethyl)piperidin-4-yl]-2-phenyl-1H-indole;
3-[1-(2-(3-chlorophenyl)ethyl)piperidin-4-yl]-2-phenyl-1H-indole;
3-[1-(2-(4-iodophenyl)ethyl)piperidin-4-yl]-2-phenyl-1H-indole;
3-[1-(2-(3-bromophenyl)ethyl)piperidin-4-yl]-2-phenyl-1H-indole;
3-[1-(2-(4-nitrophenyl)ethyl)piperidin-4-yl]-2-phenyl-1H-indole;
3-[1-(2-(4-hydroxy-3,5-dimethoxyphenyl)ethyl)piperidin-4-yl]-2-phenyl-1H-indole;
3-[-(2-(4-hydroxyphenyl)ethyl)piperidin-4-yl]-2-phenyl-1H-indole;
3-[1-(2-(4-hydroxy-3-methoxyphenyl)ethyl)piperidin-4-yl]-2-phenyl-1H-indole;
3-[1-(3-hydroxy-3-phenylpropyl)piperidin-4-yl]-2-phenyl-1H-indole;
3-[1-(2-(3,4-difluorophenyl)ethyl)piperidin-4-yl]-2-phenyl-1H-indole;
3-[1-(2-(2-chlorophenyl)ethyl)piperidin-4-yl]-2-phenyl-1H-indole;
3-[1-(2-(2-bromophenyl)ethyl)piperidin-4-yl]-2-phenyl-1H-indole;
3-[1-(2-fluoro-2-phenylethyl)piperidin-4-yl]-2-phenyl-1H-indole;
3-[1-(2-(4-chlorophenyl)ethyl)piperidin-4-yl]-2-phenyl-1H-indole;
3-[1-(3-phenylpropyl)piperidin-4-yl]-2-phenyl-1H-indole;
6-fluoro-3-[1-(2-phenylethyl)piperidin-4-yl]-2-(2-fluorophenyl)-1H-indole;
5-fluoro-3-[1-(2-phenylethyl)piperidin-4-yl]-2-phenyl-1H-indole; and pharmaceutically acceptable salts thereof.

7. A pharmaceutical composition comprising a compound of formula I as defined in claim 1 or a pharmaceutically acceptable salt thereof in association with a pharmaceutically acceptable carrier.

8. A composition as claimed in claim 7 further comprising another anti-schizophrenic medicament.

9. A method of using a compound of formula I as defined in claim 1 or a pharmaceutically acceptable salt thereof for the manufacture of a medicament for the treatment of psychotic disorders comprising the step of mixing said compound or a pharmaceutically acceptable salt thereof with a pharmaceutically acceptable carrier.

10. A process for the preparation of a compound of Formula I as claimed in claim 1 which comprises one or more steps selected from steps (A)–(E):

(A) attaching the $R^1$ moiety to a compound of formula III:

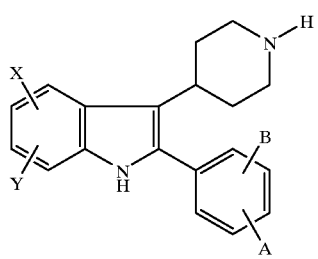

(III)

wherein A, B, X and Y are as defined in claim 1; or (B) reducing a compound of formula V:

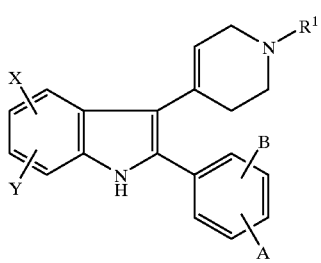

(V)

wherein A, B, X, Y and $R^1$ are as defined in claim 1; or (C) reacting a compound of formula VIII or an acid addition salt thereof with a compound of formula IX:

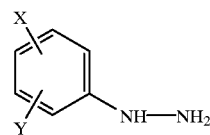

(VIII)

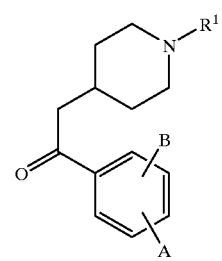

(IX)

wherein A, B, X, Y and $R^1$ are as defined in claim 1; or (D) reacting a compound of formula X with a compound of formula XI:

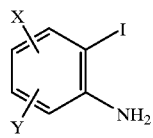

(X)

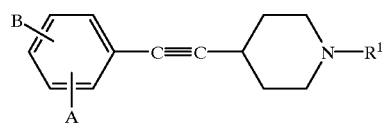

(XI)

wherein A, B, X, Y and $R^1$ are as defined in claim 1 in the presence of a transition metal catalyst; and (E) subsequently, where required, converting a compound of formula I initally obtained into a further compound of formula I by conventional methods.

11. A compound of formula III or a pharmaceutically acceptable salt thereof:

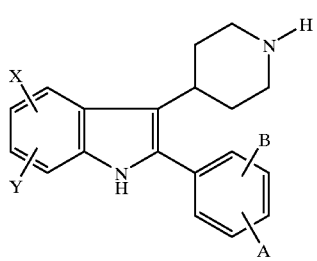

(III)

wherein A, B, X and Y are as defined in claim 1.

12. A compound of formula V or a pharmaceutically acceptable salt thereof:

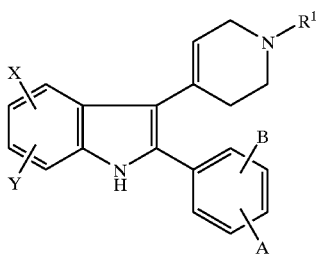

(V)

wherein A, B, X, Y and $R^1$ are as defined in claim 1.

13. A method for the treatment of psychotic disorders which comprises administering to a patient in need of such treatment an effective amount of a compound of formula I as defined in claim 1 or a pharmaceutically acceptable salt thereof.

* * * * *